US 6,632,184 B1

(12) United States Patent
Truwit

(10) Patent No.: US 6,632,184 B1
(45) Date of Patent: Oct. 14, 2003

(54) METHOD AND DEVICE FOR DEFLECTING A PROBE

(75) Inventor: Charles L. Truwit, Wayzata, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/502,991

(22) Filed: Feb. 11, 2000

(51) Int. Cl.$^7$ .......................... A61B 5/00; A61M 25/00
(52) U.S. Cl. ....................................... 600/585; 600/434
(58) Field of Search ................................ 600/434, 435, 600/585

(56) References Cited

U.S. PATENT DOCUMENTS

| | | | |
|---|---|---|---|
| 4,578,061 A | | 3/1986 | Lemelson .................... 604/164 |
| 4,769,005 A | | 9/1988 | Ginsburg et al. ............. 604/53 |
| 5,345,937 A | * | 9/1994 | Middleman et al. ......... 600/585 |
| 5,486,161 A | | 1/1996 | Lax et al. ..................... 604/22 |
| 5,707,389 A | | 1/1998 | Louw et al. .................. 606/200 |
| 5,800,389 A | | 9/1998 | Burney et al. ................ 604/93 |
| 6,120,457 A | * | 9/2000 | Coombes et al. ............ 600/486 |
| 6,217,527 B1 | * | 4/2001 | Selmon et al. ............... 600/585 |

FOREIGN PATENT DOCUMENTS

| | | | |
|---|---|---|---|
| DE | 4109205 | 9/1992 | .......... A61M/36/12 |
| WO | 99/30764 | 6/1999 | .......... A61M/25/01 |

* cited by examiner

*Primary Examiner*—Charles A Marmor, II
(74) *Attorney, Agent, or Firm*—Schwegman, Lundberg, Woessner & Kluth, P.A.

(57) ABSTRACT

A probe deflection device includes an outer tube and an inner tube. The outer tube is fabricated from an magnetic resonance (MR) compatible material. The inner tube is fabricated from a resilient material having a memory. The inner tube is shaped prior to insertion into the outer tube. To use the probe deflection device, the distal end of the outer tube is located in a biological subject near a target area. The shaped inner tube is inserted into the outer tube and extends into the target area. The shaped inner tube allows the inner tube to extend into a target area in the biological subject that is off-axis from the outer tube. A probe is inserted into the inner tube. The inner tube and the outer tube are removed from the biological subject leaving the probe embedded in the target area. Alternatively, the outer tube includes an controllable closure having an off-axis exit hole. The inner tube enters the biological subject through the off axis exit hole. A probe is inserted into the inner tube. The closure is set to the open position, which creates a slot that enhances the exit hole. The inner tube is retracted into the outer tube without deflecting the probe. The closure is set to the closed position and the outer tube is removed from the biological subject leaving the embedded probe.

12 Claims, 5 Drawing Sheets

METHOD AND DEVICE FOR DEFLECTING A PROBE

FIELD

This invention relates to inserting a probe into a biological subject, and more particularly to inserting a probe into a difficult to reach area in a biological subject.

BACKGROUND

A probe is a small object that can be inserted into a biological subject. Probes perform a variety functions. For example, some probes detect energy in a target area of a biological subject. Other probes deliver energy to a target area. Leads including electrodes inserted into a human heart provide a conductive path to the heart. Leads including electrodes inserted into a human brain provide a conductive path to the brain. Fiber optic cables inserted into a biological subject provide an optical path for viewing or ablating a target area.

One method of inserting a probe into a biological subject includes inserting a straight tube or cannula into the biological subject. The distal end of the cannula is positioned near a target area. A probe is inserted into the cannula and pushed into the target area. Finally, the cannula is removed from the biological subject leaving the inserted probe positioned in the target area.

This method is useful for inserting a probe into a target area that lies on an unobstructed straight line path from the surface of the biological subject to the target area. Unfortunately, this method is not suitable for inserting a probe into a target area in which the straight line path includes biological structures that are damaged by the insertion of a cannula or in which the target's orientation is different than the preferred trajectory of the probe.

Many areas of interest in a biological subject are located in the subject such that a straight line path from the surface of the subject passes through a biological structure that would be damaged by the insertion of the cannula. For example, the straight line path from the surface of a human subject that passes through the subthalamic nucleus along its longitudinal axis includes the lower forehead and occipital orbit. Aside from cosmetic reasons, many critical structures lie along the path and would damaged by an incision.

For these and other reasons there is a need for the present invention.

SUMMARY

The present invention provides a device for deflecting a probe. The device includes an outer tube having an opening at or near the distal end and an inner tube capable of sliding within the outer tube. The inner tube has material properties such that as the inner tube slides beyond the distal end of the outer tube, the inner tube follows a desired travel path. The distal end of the outer tube may be designed to encourage deflection of the inner tube as the inner tube moves beyond the distal end of the outer tube. This and many other embodiments are described in more detail below.

DESCRIPTION

Figure 1A:
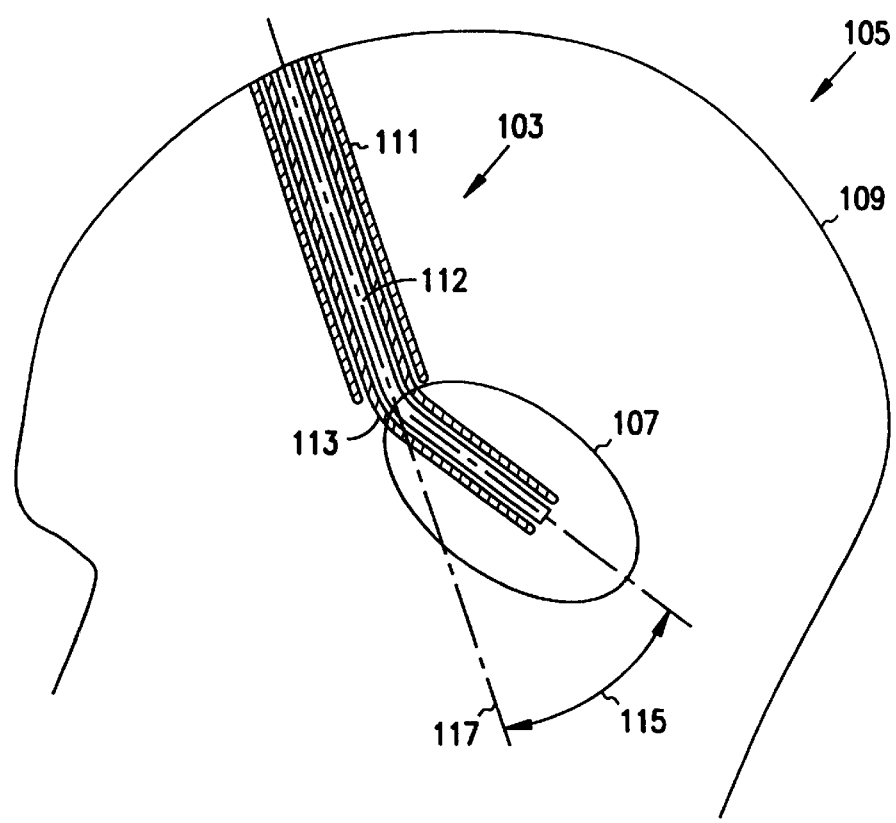
FIG. 1A is an illustration of a cross-sectional view of one embodiment of a probe deflection device including a stylet inserted into a biological subject.

In the following detailed description of the invention reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

The present invention provides a device for deflecting a probe during the insertion of the probe into a difficult to reach target area of a biological subject. The present invention also provides a method for accurately orienting a probe deflection device in a biological subject and a method for deflecting a probe in a biological subject.

FIG. 1A is an illustration of a cross-sectional view of one embodiment of probe deflection device 103 inserted into biological subject 105. Biological subject 105 includes subthalamic nucleus 107 located in the interior of skull 109. In this example, subthalamic nucleus 107 is a target area for probe deflection device 103. In one embodiment, probe deflection device 103 includes outer tube 111 and inner tube 113. Stylet 112 is shown inserted in inner tube 113. Outer tube 111 is typically a cannula suitable for insertion into a human brain. Outer tube 111 is inserted into biological subject 105 through a hole in skull 109 using a stylet. The distal end of outer tube 111 is located at a distance of about 1.3 centimeters from an axial end of subthalamic nucleus 107. The longitudinal axis of subthalamic nucleus 107 makes an angle 115 of about thirty degrees with longitudinal axis 117 of outer tube 111.

Figure 1B:
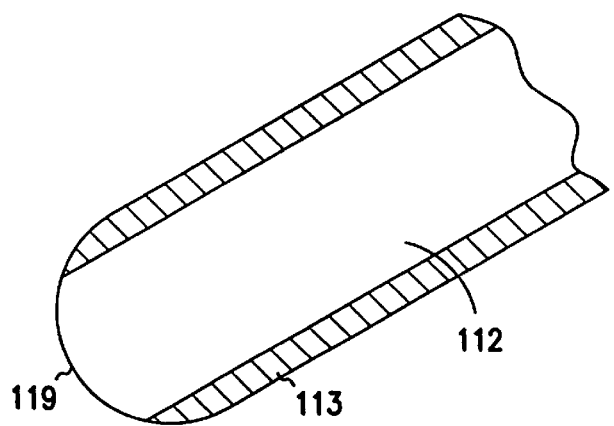
FIG. 1B is an illustration of a cross-sectional view of one embodiment of a smooth blunt tip formed when a stylet is fully inserted into an inner tube.

Inner tube 113 is fabricated from a material having material properties that permit inner tube 113 to follow a desired travel path. For example, inner tube 113, in one embodiment, is fabricated from a resilient material having a memory. To position inner tube 113 in subthalamic nucleus 107, in one embodiment, a sequence of operations is performed. First, inner tube 113 is shaped to have a bend of about 150 degrees at a point located 1.3 centimeters from the distal end of outer tube 111. Second, stylet 112 is inserted into inner tube 113. Stylet 112 has a blunt tip such that when fully inserted into inner tube 113, the inner tube distal end and the blunt tip form smooth blunt tip 119 as shown in FIG. 1B. Third, stylet 112 and inner tube 113 are inserted into outer tube 111 and pushed into subthalamic nucleus 107.

Figure 1C:
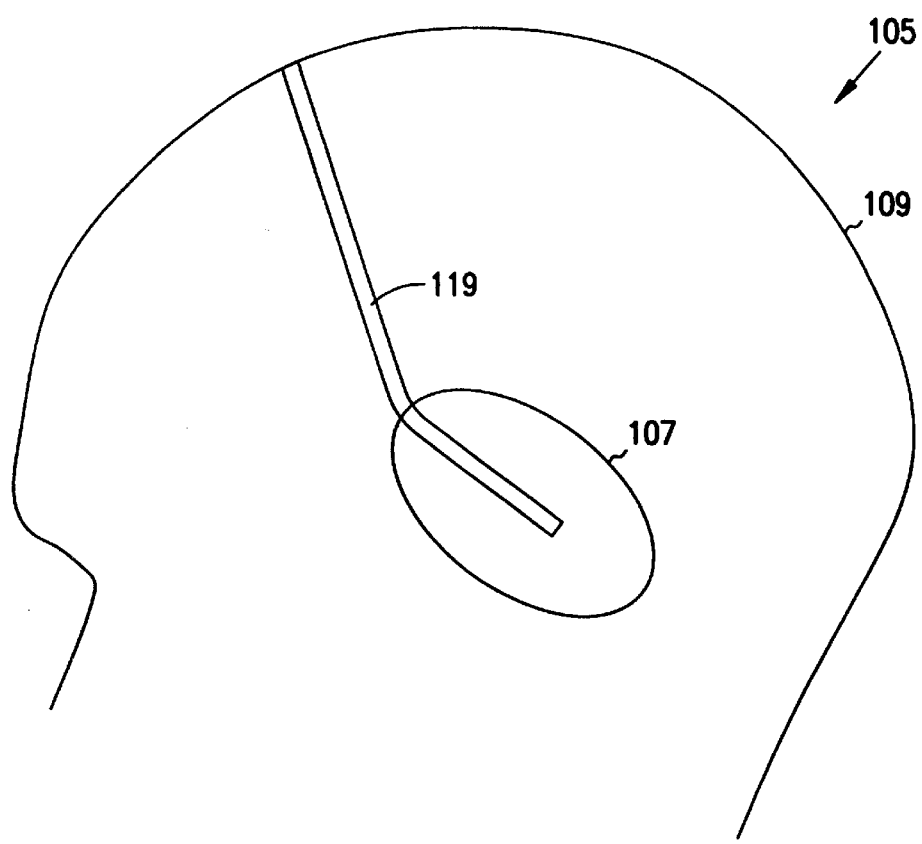
FIG. 1C is an illustration of a cross-sectional view of one embodiment of a probe embedded in a biological subject.
Figure 2:
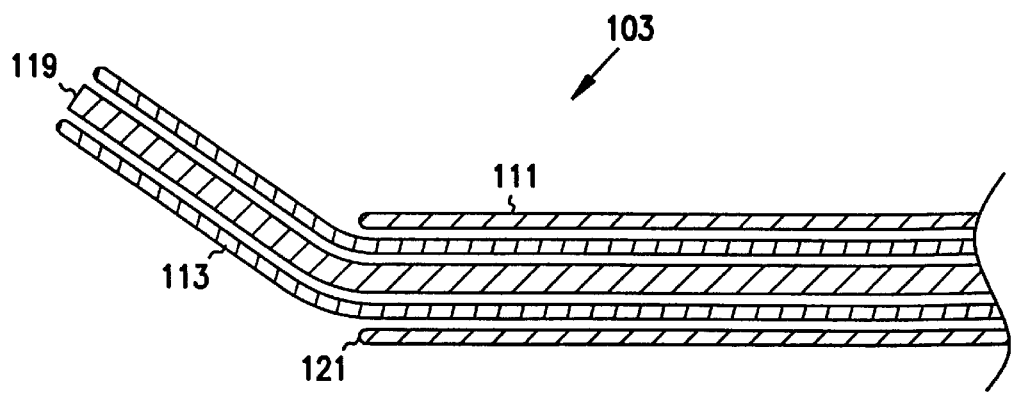
FIG. 2 is a cross-sectional illustration of one embodiment of a probe deflection device including a probe.

To position probe 119, shown in FIG. 2, in biological subject 105, a second sequence of operations is performed. First, stylet 112 is extracted from inner tube 113. Second, probe 119 is inserted into inner tube 113, effectively replacing stylet 112 in FIG. 1A. This positions probe 119 along the longitudinal axis of subthalamic nucleus 107. Third, inner tube 113 is retracted from the subthalamic nucleus into outer tube 111. Finally, inner tube 113 and outer tube 111 are retracted together from biological subject 105, leaving probe 119 embedded in biological subject 105 and subthalamic nucleus 107, as shown in FIG. 1C.

Any imaging system capable of imaging a biological subject may be used in positioning probe deflection device 103. For example, computerized tomography (CT) systems and magnetic resonance (MR) systems may be used in positioning deflection device 103 in biological subjects.

FIG. 2 is a cross-sectional illustration of one embodiment of probe deflection device 103 including probe 119. Probe deflection device 103 includes outer tube 111 and inner tube 113. In one embodiment illustrated in FIG. 2, inner tube 113 and probe 119 are shown extending beyond distal end 121 of outer tube 111.

Outer tube 111, after insertion into a biological subject, provides a path or channel from the surface of the biological subject to a target area. Outer tube 111 is preferably a tube, such as a cannula, suitable for insertion into a biological subject. The dimensions of outer tube 111 are selected to be compatible with the dimensions of probe 119 selected for insertion into the biological subject. For example, for the insertion of a deep brain stimulator (DBS) having a diameter of about 0.050 inches, outer tube 111 has an inside diameter of about 0.074 inches and an outside diameter of about 0.088 inches. These dimensions permit the insertion of inner tube 113 and probe 119 into outer tube 111. Outer tube 111, in one embodiment, is fabricated from a magnetic resonance (MR) compatible material, such as titanium. Alternatively, outer tube 111 is fabricated from a ceramic material. Fabricating outer tube 111 from an MR compatible material makes outer tube 111 suitable for use in connection with MR imaging systems.

Inner tube 113 is slidable and rotatable within outer tube 111, and when introduced into a biological subject, inner tube 113 extends from distal end 121 of outer tube 111 into the target area of the biological subject. The target area is the intended location in the biological subject for the distal end of probe 119. Inner tube 113 is fabricated from a flexible material. In one embodiment, inner tube 113 is fabricated from a resilient material having a memory. Nitinol is one example of a material suitable for use in connection with the present invention. Fabricating inner tube 113 from a resilient material having a memory allows programming inner tube 113 prior to insertion into outer tube 111. Preprogramming inner tube 113 involves bending inner tube 113 to a shape that defines a travel path for inner tube 113 as it emerges from the distal end of outer tube 111. For example, if the desired travel path is 1.3 centimeters at an angle of thirty degrees from the longitudinal axis of outer tube 111, then a one-hundred and fifty degree bend is formed in inner tube 113 at a point located about 1.3 centimeters from the distal end of inner tube 113. In this way, after inner tube 113 is inserted in outer tube 111 such that the distal end of inner tube 113 extends about 1.3 centimeters beyond the distal end of inner tube 113, inner tube 113 defines a deflected travel path for probe 119 of about thirty degrees from the longitudinal axis of outer tube 111.

Inner tube 113, in one embodiment, is inserted into a biological subject along with stylet 112 shown in FIG. 1A. To avoid cutting tissue in the biological subject, the distal end of inner tube 113 is shaped to provide a smooth surface when combined with the blunt tip stylet. The outer edges of the distal end of inner tube 113 are shaped by smoothing, rounding, or beveling. A smooth surface allows inner tube 113 to tunnel through the tissue of biological subject 105 without damaging the tissue.

A probe is a small object that can be inserted into a biological subject. Probes are not limited to a particular type of object. Probes are also not limited to a class of objects that perform a particular function. For example, leads, catheters, and fiber optic cables are all probes. Probe 119, in one embodiment, is a thin strand of material. Any material capable of being extended to the distal end of inner tube 113 is capable of being inserted into a biological subject using probe deflection device 103. In one embodiment, probe 119 is a deep brain-stimulator (DBS). In an alternate embodiment, probe 119 is a fiber optic cable. In still another alternate embodiment, probe 119 is a conductive element combined with a fiber optic cable.

Probe 119, in an alternate embodiment, is shaped to replace a stylet for the insertion of inner tube 113 into a biological subject. For probe 119 having sufficient stiffness to function as a stylet, the distal tip of probe 119 is shaped to provide a smooth surface when combined with inner tube 113. Using probe 119 to replace a stylet reduces the number of steps and the time required to insert probe 119 into a biological subject.

Probe deflection device 103 is useful for inserting a probe into a target area of a biological subject when the target area is located off axis from the longitudinal axis of outer tube 111. For example, FIG. 1 shows subthalamic nucleus 107 located off axis from longitudinal axis 117 of outer tube 111. To provide a channel or path to the off axis target area, a bend is formed in inner tube 113. In one embodiment, the bend is formed having an angle of about one-hundred and fifty degrees at a point about 1.3 centimeters from the end of the inner tube. Inner tube 113 is inserted in outer tube 111 such that the bend extends beyond the distal end of the outer tube 111. Probe 119 is inserted in inner tube 113 such that probe 119 extends beyond the end of the outer tube 111 and into the target area. Finally, inner tube 113 is removed from outer tube 111 without deflecting probe 119.

In an alternate embodiment, the method described above is modified when probe 119 is required to be precisely positioned in a target area. After insertion into the biological subject, the relationship between inner tube 113 and the target area is viewed using an imaging method, such as MR imaging. Any alignment error is identified by comparing the actual location of probe 119 with the expected: location. If the alignment error exceeds a predetermined value, then inner tube 113 is at least partially retracted into outer tube 111, rotated to correct the alignment error, and reinserted into the target area. If necessary, the MR image is examined after reinsertion to verify that inner tube 113 is properly aligned. The process is repeated as many times as necessary to achieve the proper alignment of probe 119 in the target area.

Figure 3A:
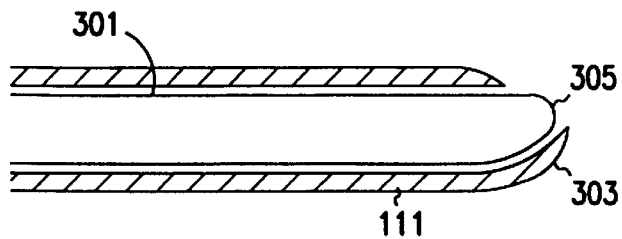
FIGS. 3A, 3B, 3C, and 3D are cross-sectional illustrations of an alternate embodiment of a probe deflection device.
Figure 3B:
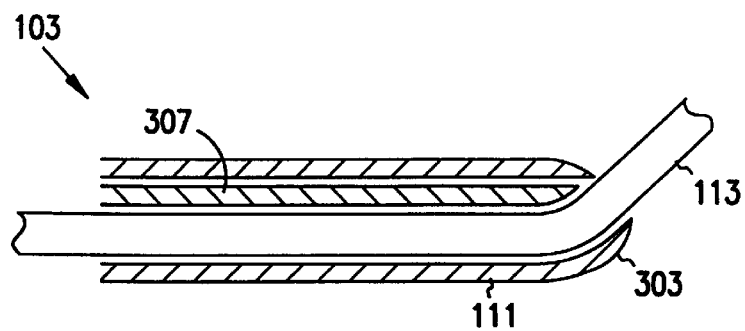
Figure 3C:
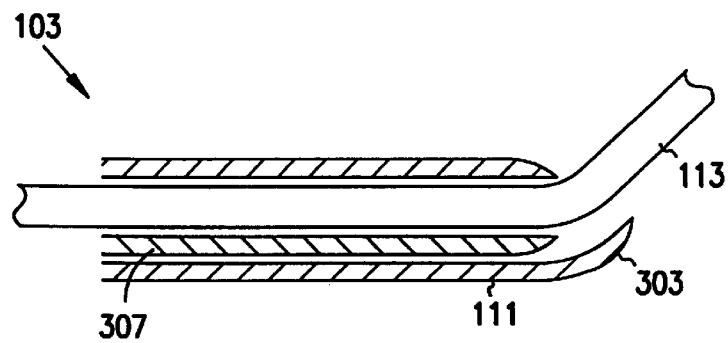

FIGS. 3A, 3B, and 3C are cross-sectional illustrations of alternate embodiments of probe deflection device 103. FIG. 3A shows a cross-sectional side view of stylet 301 inserted in outer tube 111. In this embodiment, outer tube 111 is more oval than round and includes a curved distal tip 303 for deflecting inner tube 113 along a travel path located off the longitudinal axis of outer tube 111. Curved distal tip 303 is preferably shaped such that when stylet 301 is fully inserted in outer tube 111, the blunt tip of stylet 301 and curved distal tip 303 form a smooth blunt tip 305. Smooth blunt tip 305 allows outer tube 111 to be inserted into a biological subject without damaging the tissue of the subject.

FIG. 3B shows a cross-sectional side view of inner tube 113 extending beyond curved distal tip 303 along an off-axis travel path. During the insertion of inner tube 113 into outer tube 111, spacer 307 is positioned to force inner tube 113 against the curved section of curved distal tip 303. Spacer 307 is preferably fabricated from an MR compatible material, such as titanium. Alternatively, spacer 307 is fabricated from a ceramic material. In one embodiment, spacer 307 has a crescent shape cross-sectional profile.

FIG. 3C shows a cross-sectional side view of inner tube 113 prior to the retraction of inner tube 113 into outer tube 111. Spacer 307 is positioned to force inner tube 113 against the straight section of curved distal tip 303. Forcing inner tube against the straight section of curved distal tip 303 permits the retraction of inner tube 113 into outer tube 111 without altering the position of a probe inserted into inner tube 113.

Figure 3D:
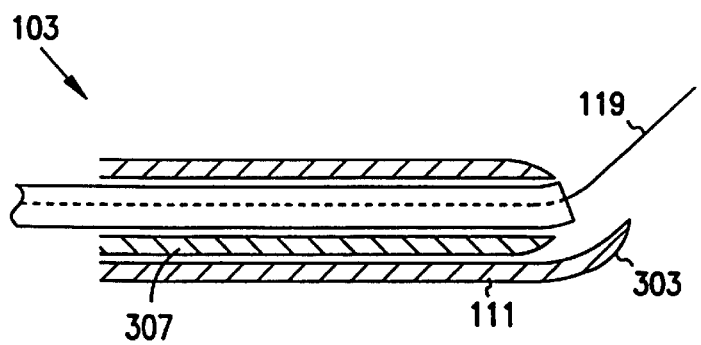

FIG. 3D shows a cross-sectional side view of inner tube 113 retracted into outer tube 111 leaving probe 119 embedded in the target area.

Figure 3E:
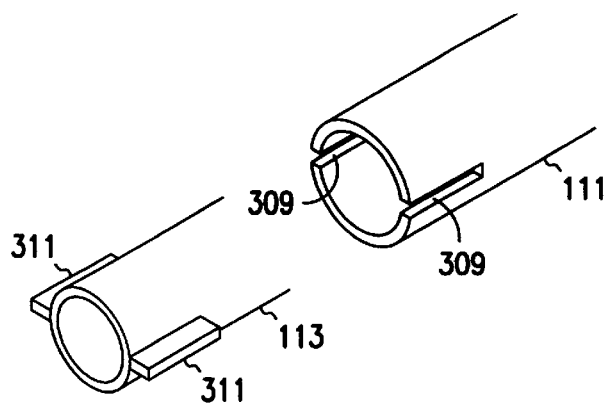
FIG. 3E is an exploded perspective view of the proximal end of the alternate embodiment of the probe deflection device shown in FIGS. 3A, 3B, 3C, and 3D.

FIG. 3E is an exploded perspective view of an alternate embodiment of the proximal end of probe deflection device 103 shown in FIGS. 3A, 3B, and 3C. Outer tube 111 includes a pair of slots 309 cut into the proximal end of outer tube 111. Inner tube 113 includes a pair of fins 311 extending out from the surface of inner tube 113. As inner tube 113 slides into outer tube 111, the pair of fins 311 fit into the pair of slots 309 and fix the rotational position of inner tube 113 within outer tube 111. Fixing the rotation position of inner tube 113 with respect to outer tube 111 permits registration of the bend in inner tube 113 with curved distal tip 303 as shown in FIG. 3B. The present invention is not limited to a slotted rotational locking system. An mechanism capable of securing inner tube 113 within outer tube 111 is suitable for use in connection with the present invention.

Figure 4A:
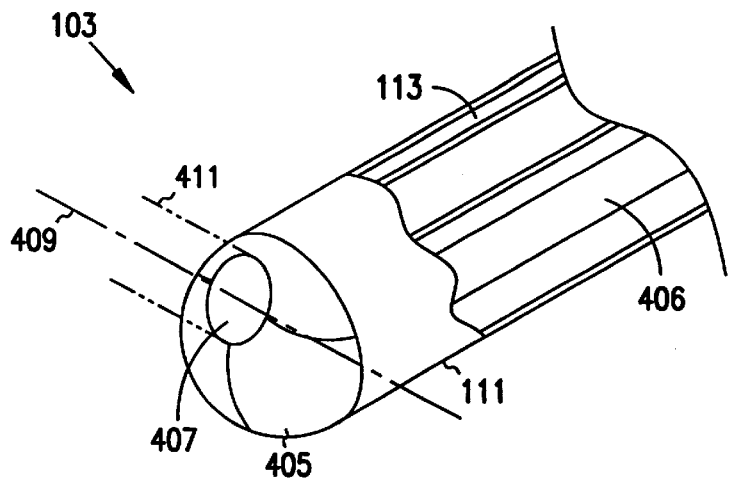
FIG. 4A is a partially cutaway perspective view of an alternate embodiment of a probe deflection device including a closure.
Figure 4B:
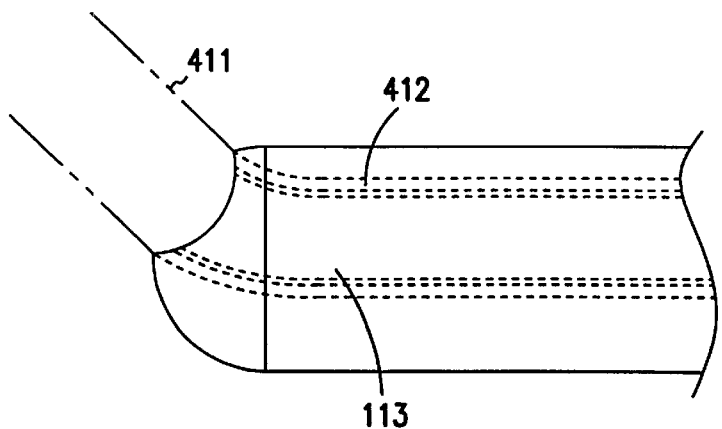
FIG. 4B is a side view of one embodiment of an outer tube showing a channel.

FIG. 4A is a partially cutaway perspective view of an alternate embodiment of probe deflection device 103. Probe deflection device 103 includes outer tube 111, inner tube 113, and closure 405 including actuator arm 406. In one embodiment, outer tube 111, inner tube 113, closure 405, and actuator arm 406 are fabricated from an MR-compatible material, such as titanium. Closure 405 includes exit hole 407 having center line 409 defining travel path 411 for inner tube 113. Exit hole 407 of closure 405 may be covered by a thin outer sheath during the insertion of outer tube 111 into a biological subject. FIG. 4B is a side view of probe deflection device 103 showing the hidden lines of channel 409 that feed inner tube 113 into travel path 411.

Figure 4C:
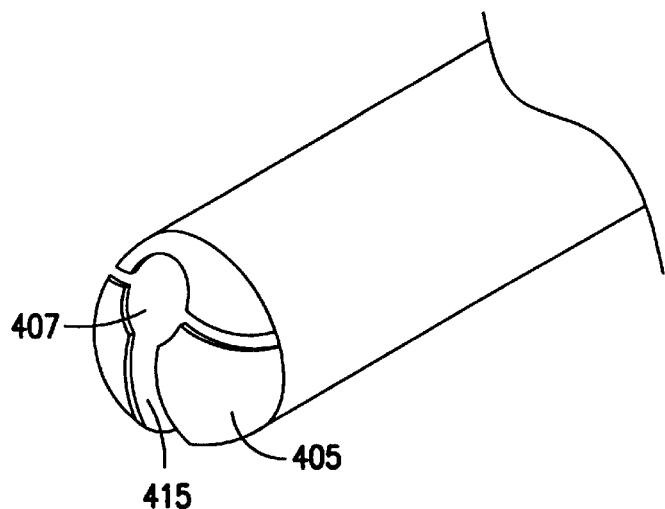
FIG. 4C is a perspective view of one embodiment of the closure shown in FIG. 4A showing the closure in the open state.
Figure 4D:
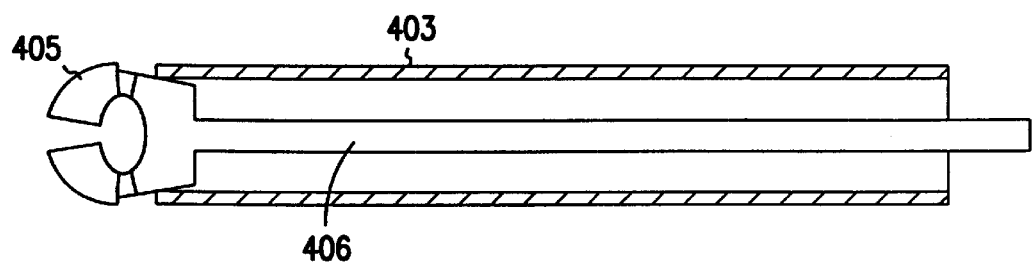
FIG. 4D is an illustration showing a cutaway top view of one embodiment of the closure shown in FIG. 4A illustrating the closure in the open state.

FIG. 4C is a perspective view of closure 405 of FIG. 4A showing closure 405 in the open position. As can be seen in FIG. 4D, actuator arm 405, in one embodiment, is accessible at the proximal end of outer tube 403. Actuator arm 406 controls the opening and closing of closure 405, and as outer tube 403 is pulled away from closure 405, closure 405 moves to an open position. Referring again to FIG. 4C, in the open position, closure 405 includes slot 415 which intersects exit hole 407. Slot 415 provides an enhanced path for inner tube 113 during the retraction of inner tube 113 into outer tube 111. The enhanced path enables the retraction of inner tube 113 into outer tube 111 without deflecting a probe introduced into inner tube 113.

Figure 5:
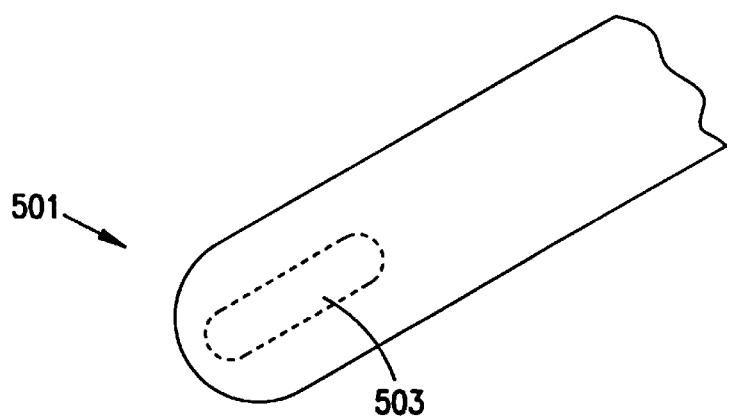
FIG. 5 is a cross-sectional view one embodiment of a stylet including marker reservoir for use in connection with the probe deflection device of FIG. 4A.

FIG. 5 is a cross-sectional side view of one embodiment of stylet 501 including imaging marker reservoir 503. Stylet 501 is suitable for use in connection with the probe deflection device 103 of FIG. 4A. In one embodiment, stylet 501 is fabricated from a flexible material, such as plastic, that is compatible with imaging systems. Imaging marker reservoir 503 is located near the tip of stylet 501 and is shaped to indicate the orientation of stylet 503. In one embodiment, imaging marker reservoir 503 has an elongated shape extending along the longitudinal axis of stylet 501. Imaging marker reservoir 503 also encapsulates an imaging contrast media, such as an iodinated contrast media for use with a CT imaging system or a paramagnetic contract media, such as gadolinium for use with an MR imaging system. Stylet 501 is not limited to the embodiment described above. In an alternate embodiment, stylet 501 is a flexible catheter filled with an imaging contrast media.

Stylet 501 is useful in orienting exit hole 507 of closure 505, as shown in FIG. 5A, in a biological subject. Outer tube 503 is inserted into the biological subject. Stylet 501 is inserted into outer tube 111 directly, or inserted into inner tube 113 before insertion into outer tube 111. As the tip of stylet 501 reaches exit hole 407, imaging marker reservoir 503 points along travel path 411. Travel path 411 is identified by examining an image of stylet 501. After identifying the projected travel path of stylet 501, outer tube 403 is rotated to correct for any error detected in the image. If the detected error is less than a predetermined value, then the orientation of outer tube 111 is left unchanged.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A probe deflection device comprising:
   an outer tube having a distal end;
   an inner tube capable of sliding within the outer tube, the inner tube having an inner tube distal end and material properties such that as the inner tube slides beyond the distal end of the outer tube, the inner tube follows a desired travel path; and
   a stylet having a smooth blunt tip such that when the stylet is fully inserted into the inner tube, the blunt tip and the inner tube distal end form a smooth blunt tip suitable for tunneling through tissue of a biological subject.

2. The probe deflection device of claim 1, wherein the outer tube is fabricated from a magnetic resonance (MR) compatible material.

3. The probe deflection device of claim 2, wherein the MR compatible material is titanium.

4. The probe deflection device of claim 1, wherein the outer tube has an inside diameter and the inner tube has an outside diameter and the inside diameter is between about 0.186 and about 0.190 centimeters and the outside diameter is between about 0.171 and about 0.174 centimeters.

5. The deflection device of claim 1, wherein the inner tube is fabricated from a flexible material.

6. The probe deflection device of claim 1, wherein the inner tube is fabricated from a resilient material having a memory.

7. The probe deflection device of claim 6, wherein the resilient material having a memory is nitinol.

8. The probe deflection device of claim 7, wherein the inner tube is capable of being rotated within the outer tube.

9. The probe deflection device of claim 1, wherein the outer tube has a length and a longitudinal axis and the desired travel path includes a segment which creates an angle of about thirty degrees with the longitudinal axis.

10. The probe deflection device of claim 1, further comprising:

a probe inserted in the inner tube.

11. The probe deflection device of claim 10, wherein the probe is an electrode.

12. The probe deflection device of claim 10, wherein the probe is a fiber optic strand.

* * * * *